United States Patent [19]

Daniel

[11] Patent Number: 5,297,538
[45] Date of Patent: Mar. 29, 1994

[54] SURGICAL RETRACTOR/COMPRESSOR

[76] Inventor: Elie C. Daniel, 402 First Ave., Mendota, Ill. 61342

[21] Appl. No.: 866,862

[22] Filed: Apr. 10, 1992

[51] Int. Cl.⁵ .................... A61B 17/02; A61B 17/28
[52] U.S. Cl. ...................................... 128/20; 128/17; 606/207; 606/208
[58] Field of Search ................ 128/17, 20; 606/105, 606/190, 205–209, 151, 191, 198, 86; 81/418, 421, 177.85, 313, 338; 433/159, 157, 4

[56] References Cited

U.S. PATENT DOCUMENTS

| 307,322 | 4/1990 | Dolwick | D24/135 |
| 1,523,022 | 12/1923 | Larson | 81/177.85 |
| 1,624,922 | 4/1927 | Broyles | 81/134 |
| 2,631,585 | 3/1953 | Siebrandt | 606/208 |
| 3,604,414 | 9/1971 | Borges | 606/105 |
| 4,502,485 | 3/1985 | Burgin | 128/20 |
| 4,574,804 | 3/1986 | Kurwa | 606/190 |
| 4,620,460 | 11/1986 | Gonzales, Jr. | 81/177.85 |
| 4,754,746 | 7/1988 | Cox | 128/20 |
| 4,896,661 | 1/1990 | Bogert et al. | 606/207 |
| 4,955,896 | 9/1990 | Freeman | 606/207 |
| 4,955,897 | 9/1990 | Ship | 606/207 |
| 5,147,369 | 9/1992 | Wagner | 606/205 |

FOREIGN PATENT DOCUMENTS

| 73094 | 1/1894 | Fed. Rep. of Germany | 606/198 |
| 1913187 | 10/1970 | Fed. Rep. of Germany | 606/198 |
| 2144041 | 5/1973 | Fed. Rep. of Germany | 606/151 |
| 3006027 | 11/1981 | Fed. Rep. of Germany | 606/208 |
| 2419063 | 10/1979 | France | 606/151 |
| 2635452 | 2/1990 | France | 606/206 |
| 313539 | of 1933 | Italy | 433/159 |
| 1553073 | 3/1990 | U.S.S.R. | 606/198 |
| 20251 | of 1914 | United Kingdom | 606/207 |
| 290799 | 1/1928 | United Kingdom | 128/17 |

Primary Examiner—Richard J. Apley
Assistant Examiner—Donna Maraglio
Attorney, Agent, or Firm—Rockey, Rifkin and Ryther

[57] ABSTRACT

The surgical instrument consists of a pair of arms of different lengths hinged together at an intermediate point for relative pivoting movement. The arms are provided with obliquely oriented handles at one end thereof. The opposite ends of the arms support removable posts having means for removably securing a plurality of different surgical heads. A variety of heads and different shaped posts are provided to facilitate retraction in a wide variety of surgical procedures. A serrated locking mechanism is also provided to lock the arms in either a retraction or compression mode.

16 Claims, 5 Drawing Sheets

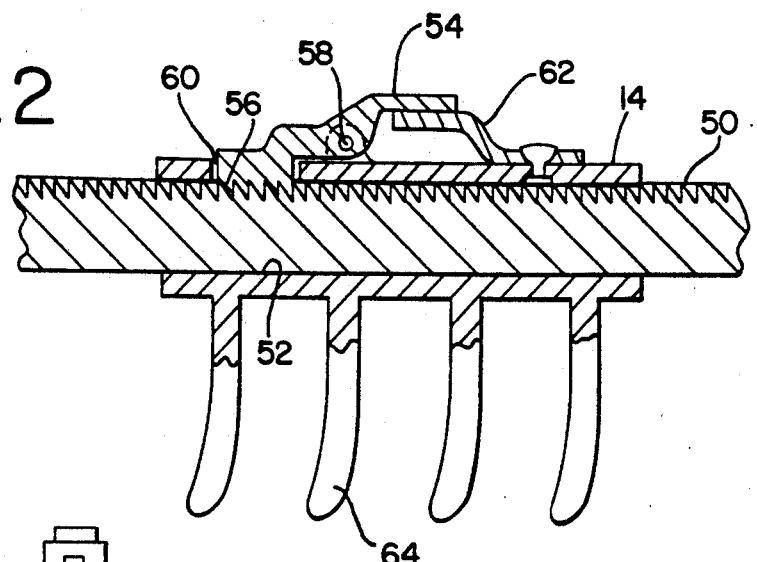
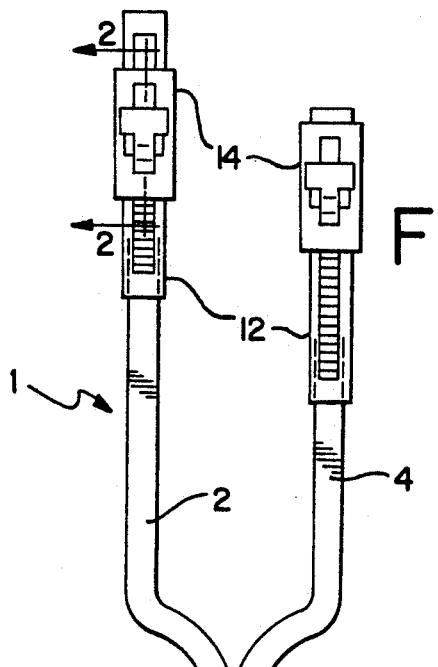
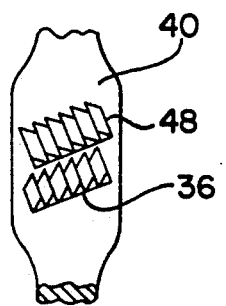
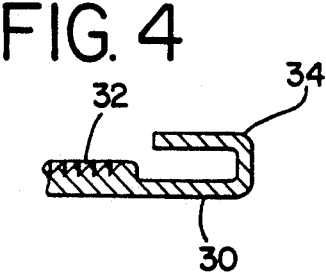
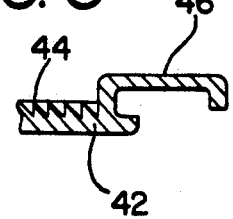
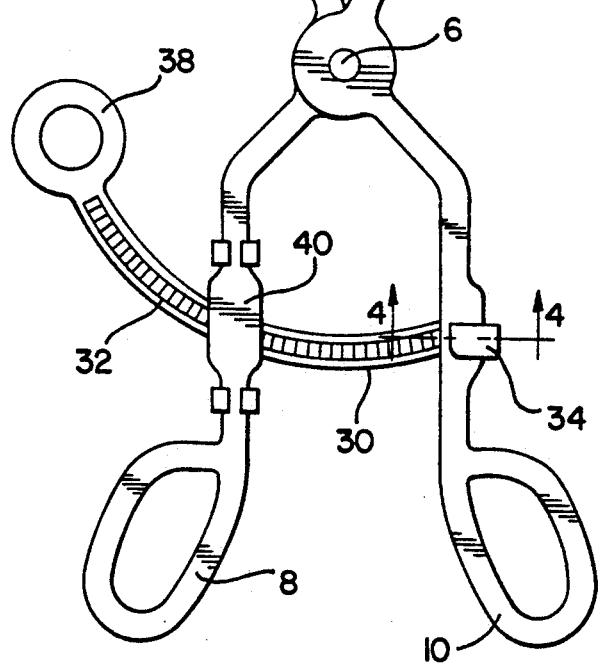

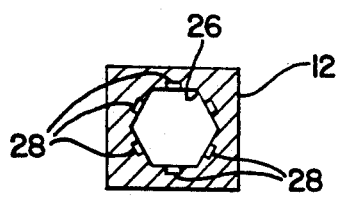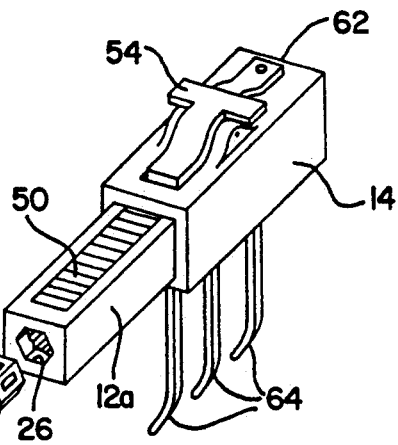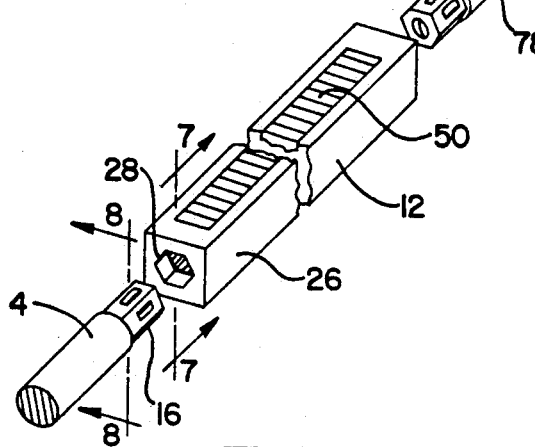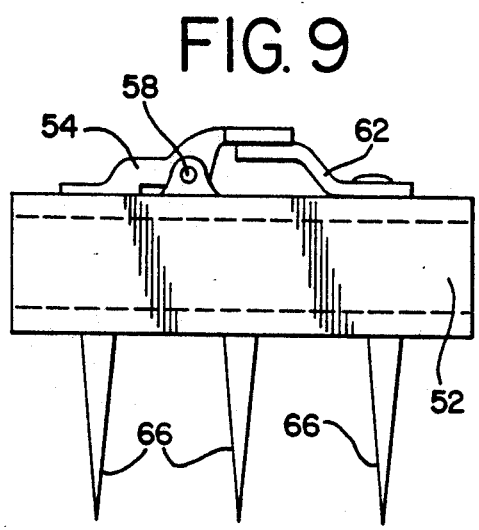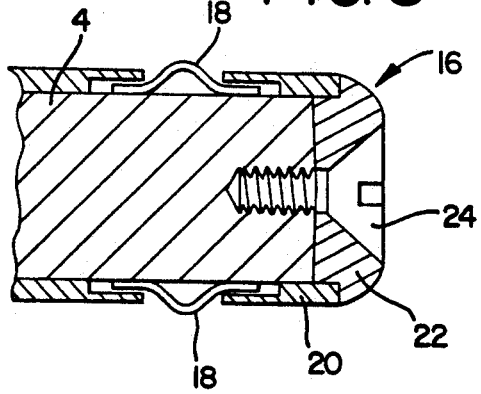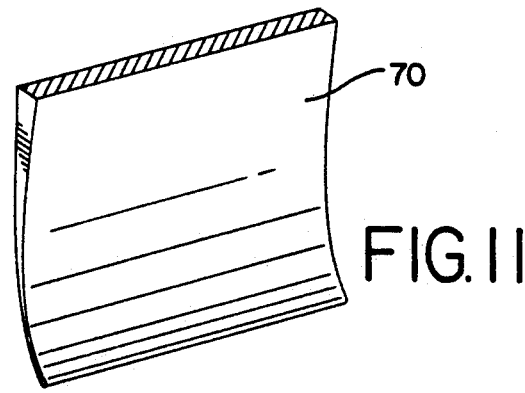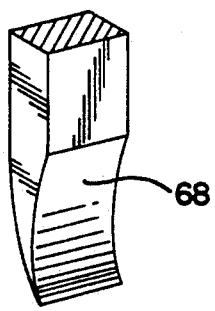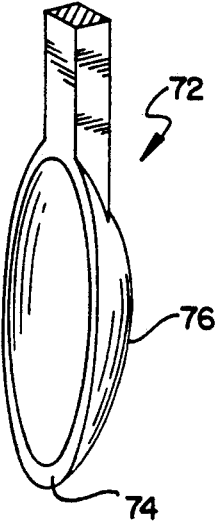

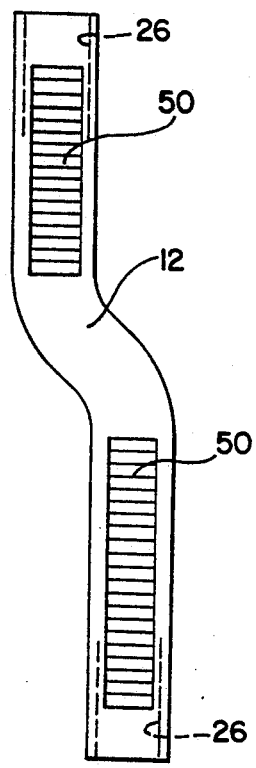
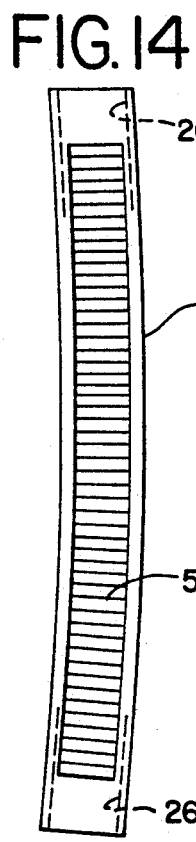
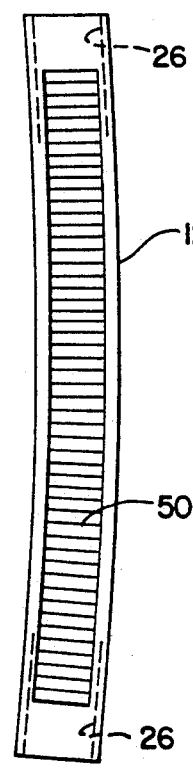
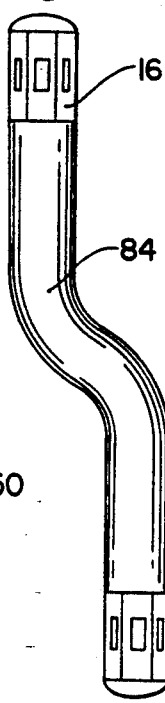
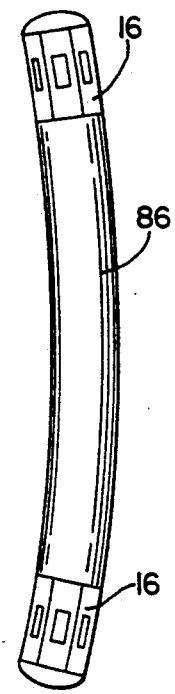
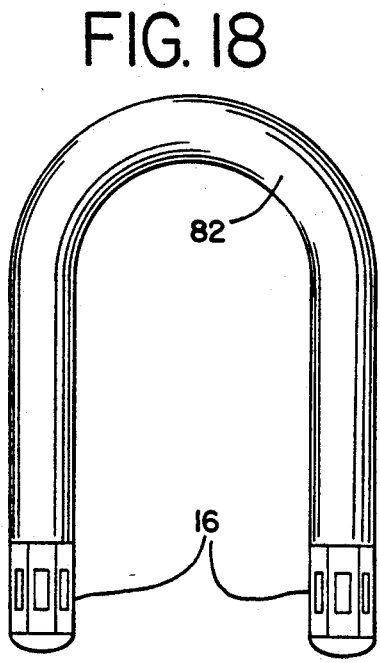
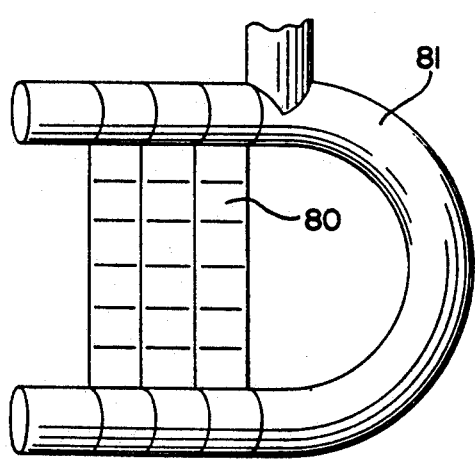

FIG. 21
FIG. 20
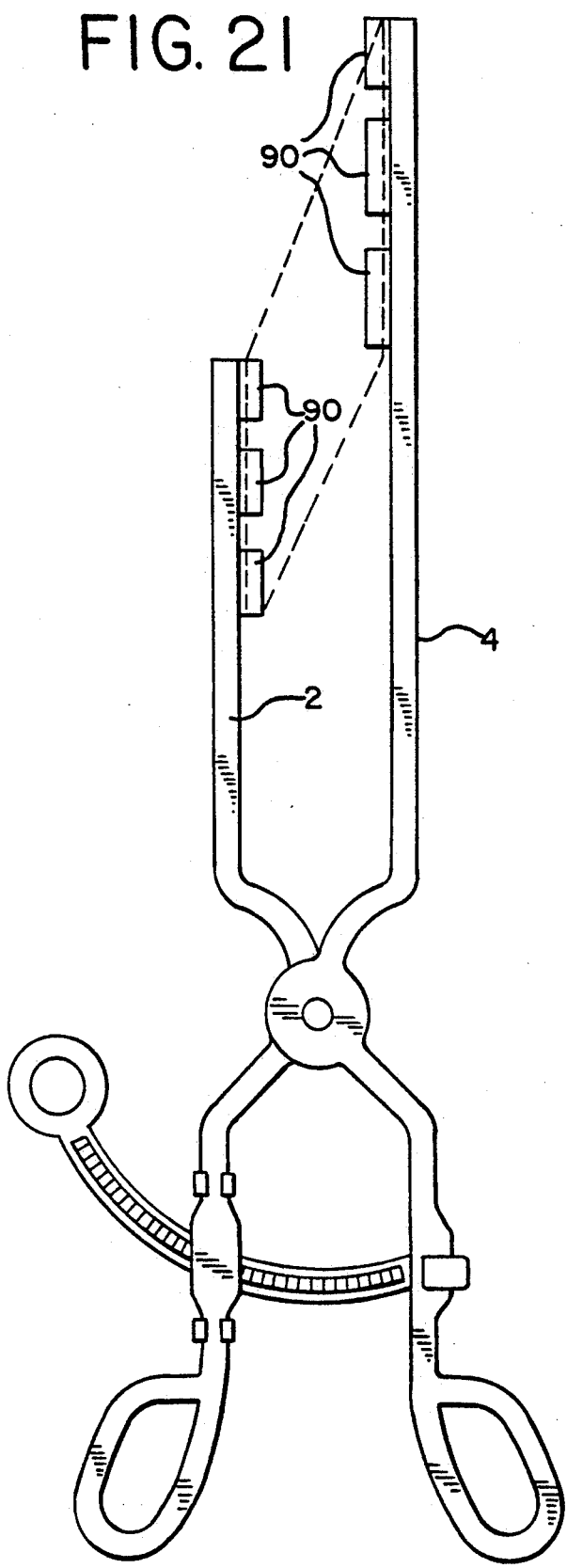
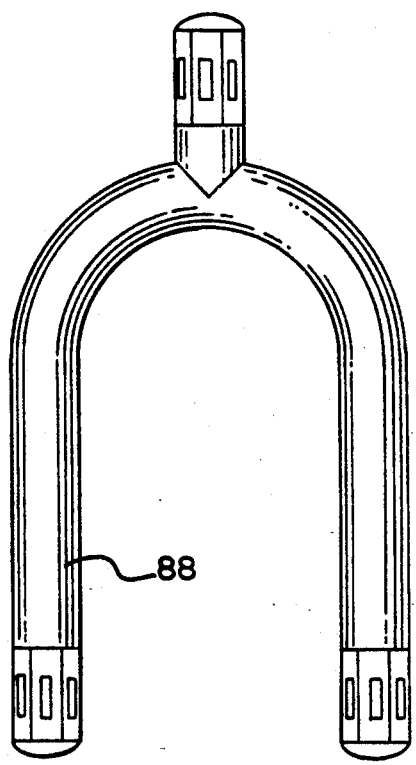

SURGICAL RETRACTOR/COMPRESSOR

BACKGROUND OF THE INVENTION

The invention relates, generally, to medical instruments and, more particularly, to a combined surgical retractor/compressor.

Retractors are used during surgery to retract tissue, spread ribs and perform similar functions. Compressors are used to compress and hold tissue, bone and the like. Both retractors and compressors typically include a pair of elongated arms pivotally connected intermediate their ends for relative motion. The arms are typically symmetrical and include either a retractor or compressor head fixed to the ends thereof designed to perform a specific surgical procedure.

While such devices are widely used, the symmetry of the arms limits their use and the fact that the heads are fixed to the arms necessitates the use of separate instruments for different surgical procedures. Moreover, retractors cannot be used for compression and compressors cannot be used for retraction. Thus, an improved surgical tool that can be used in a variety of surgical applications is desired.

SUMMARY OF THE INVENTION

The surgical instrument of the invention overcomes the above-noted shortcomings and consists of a pair of arms of different lengths hinged together at an intermediate point for relative pivoting movement. The arms are provided with obliquely oriented handles at one end thereof. The opposite ends of the arms support removable posts having means for removably securing a plurality of different retractor or compressor heads thereto. A variety of retractor and compressor heads and different shaped posts are provided to allow the instrument to be used in a wide variety of surgical procedures. Separate serrated locking mechanisms are provided to lock the arms in either a retraction or compression position.

BRIEF DESCRIPTION OF THE DRAWINGS

FIG. 1 is a side view of the retractor of the invention.

FIG. 2 is a section view of the invention taken along line 2—2 of FIG. 1.

FIG. 3 is a detailed view of one of the arms of the invention.

FIGS. 4 and 5 are partial section views of the locking mechanisms of the invention.

FIG. 6 is a partial exploded view of the invention.

FIG. 7 is a section view taken along line 7—7 of FIG. 6.

FIG. 8 is a section view taken along line 8—8 of FIG. 6.

FIGS. 9 through 12 and 19 show alternate embodiments of the retractor/compressor heads of the invention.

FIGS. 13 through 15 show alternate configurations of the post of the invention.

FIGS. 16 through 18 and 20 show alternate configurations of the connector of the invention.

FIG. 21 shows an alternate embodiment of the invention where the retractor/compressor heads are fixed to the arms.

DETAILED DESCRIPTION OF THE DRAWINGS

Figure 22:
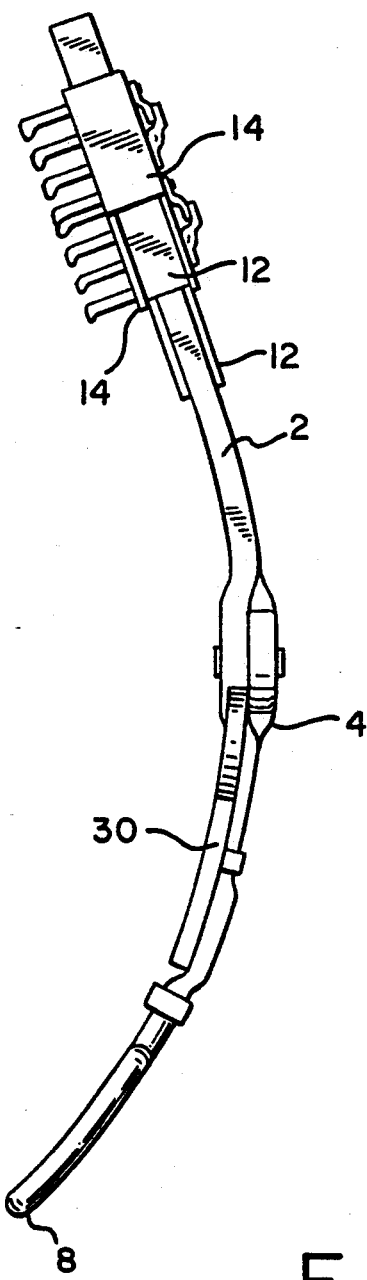
FIG. 22 shows an alternate embodiment of the invention having a curved profile.

Referring more particularly to the figures, the surgical instrument of the invention is shown generally at 1 consisting of a pair of arms 2 and 4 pivotally connected at hinge 6 such that the arms can pivot relative to one another. Arms 2 and 4 are provided with obliquely angled handles 8 and 10, respectively, to facilitate their manipulation. The arms are arranged such that when handles 8 and 10 are moved towards one another the upper portion of arms 2 and 4 are moved away from one another and vice versa. The arms 2 and 4 are also made different lengths to facilitate the manipulation of tissue and provide the surgeon greater flexibility as to how the instrument can be used. Moreover, arms 2 and 4 can be curved as shown in FIG. 22 to allow manipulation of the arms around obstructing body parts. The arms 2 and 4 support posts 12 which, in turn, support retractor/compressor heads 14 as will hereinafter be described.

Referring more particularly to FIGS. 6, 7 and 8, arms 2 and 4 include snap-fit connectors 16 at the ends thereof consisting of a plurality of leaf springs 18 mounted under sleeve 20. A cap 22 is secured to the end of arms 2 and 4 by any suitable fastener 24 to retain sleeve 20 on arms 2 and 4. Connectors 16 releasably engage receptacles 26 formed in posts 12 to removably secure posts 12 to arms 2 and 4. Receptacles 26 consists of an aperture dimensioned and shaped to be matingly engaged by snap-fit connectors 16 such that leaf springs 18 engage recesses 28 formed in the walls of receptacles 26. As will be apparent from the foregoing description, the leaf springs 18 will be compressed when connectors 16 are forced into and out of receptacles 26 and will expand when aligned with recesses 28 to lock arms 2 and 4 into posts 12. The connectors 16 and receptacles 26 are configured to prevent relative rotational movement between these elements. As illustrated, these elements have in cross-section a six-sided configuration although other arrangements such as a key and slot could be used. The use of the hexagonal receptacles 26 and connectors 16 allows the surgical heads to be located at oblique angles relative to the arms 2 and 4. It will be apparent that a greater or fewer number of sides may be used, such as an octagonal shape, to allow larger or smaller angles between positions.

Referring more particularly to FIGS. 1, 3, 4 and 5, locking mechanisms 30 and 42 ar provided for fixing the position of arms 2 and 4 relative to one another in a retraction mode or compression mode, respectively. Locking mechanism 30 includes serrations 32 and is removably fixed to arm 4 by clip 34. Serrations 32 are engageable with a corresponding set of serrations 36 formed on enlarged portion 40 of arm 2 to lock the arms in a retracting position. A loop 38 is provided at the end of member 30 to allow the instrument to be secured to a surgical drape. Locking mechanisms 30 and 42 are curved to follow the path of travel of arms 2 and 4 as they are pivoted relative to one another.

Referring to FIG. 5, a second locking mechanism 42 is provided that is identical to mechanism 30 except that serrations 44 face the opposite direction and clip 46 is configured to resist a compressive force. Locking mechanism 42 is engageable with a second set of projections 48 formed on enlarged portion 40 to lock the arms in a compressing position. Locking mechanisms 30 and 42 allow the instrument of the invention to be used as retractor and a compressor, respectively.

Posts 12 are shown in greater detail in FIGS. 2 and 13-15. One side of post 12 is provided with serrations 50 which can mate with serrations formed on retractor and compressor heads 14 as will hereinafter be described. The posts 12 include receptacles 26 at both ends such that the posts can receive connectors 16 at either end, the purpose of which will be hereinafter described.

Alternate embodiments of posts 12 are shown in FIGS. 13-15. The post can be provide with a curved profile as shown in FIGS. 14 and 15. The post, as shown in FIG. 13, can also be provided with a generally S-shape. The specific shape chosen for the post will be dictated by the application in which the instrument is used. While a number of alternate shapes for the posts have been described, it is to be understood that the post shape is not limited to those illustrated and can take any desired shape. Moreover, the lengths of the posts can be varied as desired.

The retractor and compressor heads 14 are mounted to posts 12 by the mounting mechanisms shown in FIGS. 2 and 9 consisting of a passage 52 for receiving posts 12, such that the surgical heads 14 can be removably positioned along the length of posts 12. An arm 54 having serrations 56 is pivotally connected to the outside of head 14 at hinge 58 such that serrations 56 extend through aperture 60 into passage 52. A leaf spring 62, fixed at one end to head 14, engages the end of arm 54 to force serrations 56 into engagement with serrations 50 to lock head 14 on post 12. Head 14 can be removed by pushing on arm 54 to overcome the force of spring 62 and remove serrations 56 from engagement with serrations 50. It should be noted that heads 14 could be made integrally with posts 12 if desired such that the post and head could be secured to the arms as a unit.

The retractor heads 14 include members 64 for gripping tissue. Members 64 can consist of spikes 66 (FIG. 9) or narrow plates 68 (FIG. 10) for retracting bone. Alternatively, members 64 could be replaced by wide plates 70 for muscular, vascular or neurological work as shown in FIG. 11.

Another embodiment of the tissue gripping members is shown in FIG. 12 and consists of a segment of a sphere 72, the edge 74 of which can be used to move metatarsals or metacarpals apart or for morton neuromas and tendon work. The spherical surface 76 can be used to retract tissues and for hemostasis. Retractor/compressor heads provided with these and other tissue gripping members can be selected by the surgeon for performing a wide variety of tasks.

Another embodiment of the invention is shown in FIG. 19, where the tissue gripping member could include a net 80 mounted on a U-shaped retainer 81. The net can be used to handle softer tissue to minimize damage to the tissue.

As shown in FIG. 6, separate connector rods 78 having snap-fit connectors 16 at either end thereof can be inserted into receptacle 26 of post 12 and a second post 12a can be mounted on connector rod 78. Additional retractor and compressor heads can be mounted on this additional post as well to provide the surgeon with maximum flexibility.

Connectors other than the straight connector rod 78 can also be used to allow the surgeon to obtain different retractor configurations. For example, the connector rods can have an S-shaped design 84 or a curved design 86 as illustrated in FIGS. 16 and 17. Another embodiment of the connector rods is shown in FIG. 18 and consists of a generally U-shaped rod 82. Finally, the connector rod 88 can be configured as a Y-shaped connection as shown in FIG. 20.

Referring more particularly to FIG. 21, the instrument of the invention is shown with the retractor heads 90 fixed permanently to arms 2 and 4 by any suitable method such as welding. In this embodiment, although the retractor heads 90 cannot be removed from arms 2 and 4, the manipulation of tissue is facilitated because the arms are made different lengths. In use, an instrument with different length arms will, when used as a retractor, create an opening as shown in FIG. 21 in dashed lines. As is apparent, this opening provides the surgeon a different view of the surgery situs from that provided where the arms are of equal length.

Figure 23:
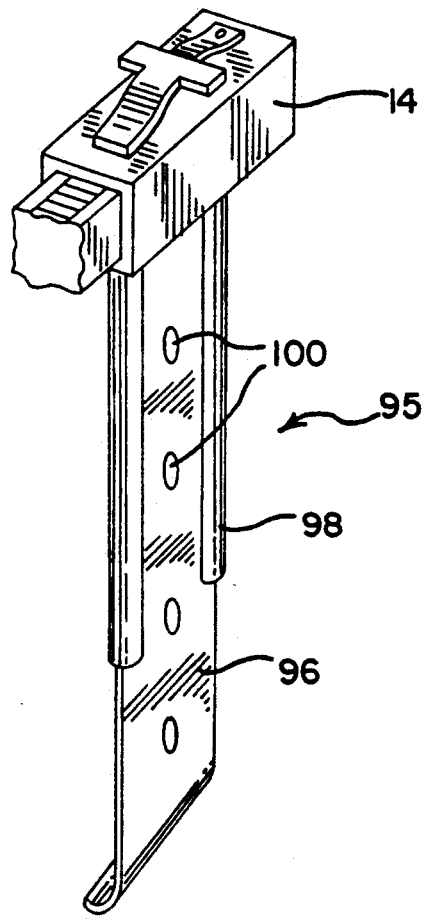
FIGS. 23 and 24 show a further modification of the retractor heads of the invention.
Figure 24:
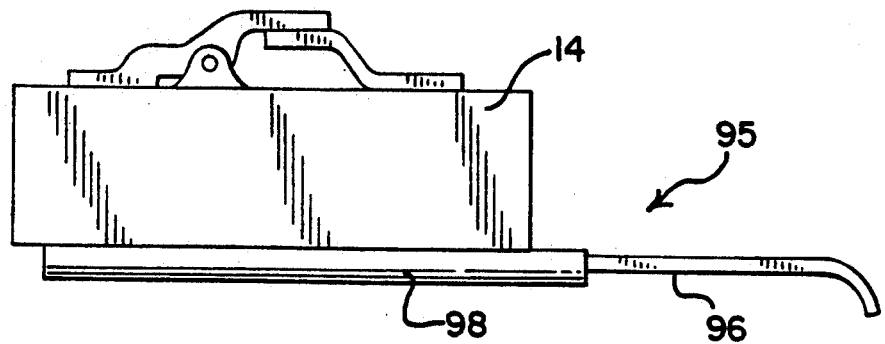

Referring more particularly to FIGS. 23 and 24, the retractor head 14 can include an extensible/retractable tissue contacting member 95 which includes a slide member 96 slidably supported in retaining member 98. In the illustrated embodiment retaining member 98 is formed to create a channel in which the slide member 96 can slide. The member 96 is maintained in position in member 98 by the frictional forces between the channel of retaining member 98 and the slide member 96. Slide member 96 can be provided with stops which engage the bottom edge of retaining member 98 to prevent the slide member 96 from coming out of retaining member 98. Depressions 100 can be formed in slide member 96 to provide the surgeon a means for securely moving the slide member. Member 95 can be mounted to extend from the retractor head 14 at a 90° angle as shown in FIG. 23 or can be mounted flush to the head as shown in FIG. 24. The slide member 96 can be formed with any suitable tissue engaging surface.

As will be apparent from the foregoing description, the retractor of the invention can be configured as desired by the surgeon to perform virtually any retraction or compression procedure. Although the invention has been described in some detail with respect to the drawings, it will be understood that the foregoing description was offered merely by way of example and that numerous changes can be made to the construction and details of the device without departing from the spirit and scope of the invention.

What is claimed is:

1. A surgical instrument comprising:
   (a) first and second arms pivotally secured together at an intermediate point to allow relative pivoting movement;
   (b) a plurality of posts, each post including a first set of serrations extending along the partial length thereof;
   (c) means for removably securing said posts to said arms whereby different posts can be secured to said arms depending on the surgical procedure to be performed;
   (d) a plurality of surgical heads including means for contacting tissue; and
   (e) means for removably securing the surgical heads to the posts including a passage extending through each surgical head for receiving the post and a second set of serrations formed on each surgical head for releasably engaging said first set of serrations such that the surgical head can be movably positioned along the length of the post whereby different surgical heads can be secured to said arms depending on the surgical procedure being performed.

2. The surgical instrument according to claim 1, wherein the means for removably securing the posts to the arms includes a receptacle on said posts for receiving mating connectors on said arms for releasably securing said arms in said receptacles.

3. The surgical instrument according to claim 2, wherein the means for removably securing the posts to the arms includes at least one leaf spring formed on the arms releasably engageable with a corresponding recess formed in the posts.

4. The surgical instrument according to claim 1, wherein said posts are straight.

5. The surgical instrument according to claim 1, wherein said posts are curved.

6. The surgical instrument according to claim 1, wherein said means for contacting tissue includes flexible netting.

7. The surgical instrument according to claim 1, wherein said means for contacting tissue includes plates.

8. The surgical instrument according to claim 1, wherein said means for contacting tissue includes spikes.

9. The surgical instrument according to claim 1, wherein said means for contacting tissue includes a segment of a sphere.

10. The surgical instrument according to claim 1, wherein the arms are curved.

11. The surgical instrument according to claim 1, further including means for locking said arms in compression or retraction comprising first and second sets of projections formed on said second arms, a first locking mechanism releasably secured to the first arm and engageable with the first set of projections on the second arm to lock the arms in a retracting position and a second locking mechanism releasably secured to the first arm and engageable with the second set of projections on the second arm to lock the arms in a compressing position.

12. The surgical instrument according to claim 1, wherein the posts support a connecting rod and the connecting rod supports another post, said another post including means for supporting surgical heads.

13. The surgical instrument according to claim 1, wherein said first and second arms are of different lengths.

14. The surgical instrument according to claim 1, wherein said means for securing said posts to said arms includes means for locking said posts to the arms at different angles such that the angle of the surgical heads relative to the arms can be varied.

15. The surgical instrument according to claim 14, wherein said means for locking fixes the posts at discrete angles relative to the arms.

16. The surgical instrument according to claim 1, wherein the means for contacting tissue includes a first member fixed to said surgical head and a second member slidable relative to the first member.

* * * * *